United States Patent [19]
Botts et al.

[11] Patent Number: 5,453,098
[45] Date of Patent: Sep. 26, 1995

[54] TWO STEP IV FLUID FLOW STOP

[75] Inventors: Charles R. Botts, San Diego, Calif.; Robert B. Cushman, Cedar Crest, N.M.; Ahmad-Maher M. Moubayed, San Diego; John Thompson, San Clemente, both of Calif.

[73] Assignee: Imed Corporation, San Diego, Calif.

[21] Appl. No.: 241,041

[22] Filed: May 9, 1994

[51] Int. Cl.[6] ............................... A61M 5/00; F16K 7/04
[52] U.S. Cl. ............................... 604/249; 604/250; 251/7
[58] Field of Search .................... 604/151, 153, 604/246, 249, 250, 256; 251/4, 7

[56]  References Cited

U.S. PATENT DOCUMENTS

| | | |
|---|---|---|
| 2,889,848 | 6/1959 | Redmer . |
| 3,189,038 | 6/1965 | Von Pechmann . |
| 4,460,358 | 7/1984 | Somerville et al. . |
| 4,586,691 | 5/1986 | Kozlow ................... 604/250 |
| 4,689,043 | 8/1987 | Bisha ...................... 604/250 |
| 4,818,190 | 4/1989 | Pelmulder et al. . |
| 4,857,048 | 8/1989 | Simons et al. . |
| 4,925,152 | 5/1990 | Huber . |
| 5,017,192 | 5/1991 | Dodge et al. . |
| 5,190,527 | 3/1993 | Hamilton et al. . |
| 5,219,327 | 6/1993 | Okada .................... 604/250 |
| 5,257,978 | 11/1993 | Haber et al. ............ 604/250 |

FOREIGN PATENT DOCUMENTS

| | | |
|---|---|---|
| 0423978A2 | 4/1991 | European Pat. Off. . |
| 0510881A2 | 10/1992 | European Pat. Off. . |
| WO93/05829 | 4/1993 | WIPO . |

*Primary Examiner*—C. Fred Rosenbaum
*Assistant Examiner*—Frank Wilkens, III
*Attorney, Agent, or Firm*—Nydegger & Associates

[57] ABSTRACT

A device for holding an IV tube in a pumping apparatus and for selectively occluding the tube when the door of the pumping apparatus is opened, to prevent free flow of fluid in the tube. The device consists of a base member to which the IV tube is attached or through which it passes, and a slide clamp which slides relative to the base member and relative to the tube. The IV tube is passed through an elongated aperture in the slide clamp, and the slide clamp is slidingly mounted on the base member. The aperture in the slide clamp has a relatively open hole at one end, through which the tube passes when the slide clamp is in one position, allowing fluid to flow through the tube. The aperture also has a relatively constricted slot at the other end, through which the tube passes when the slide clamp is in a second position, preventing fluid flow through the tube. A flexible cantilevered arm on the base interlocks with a locking projection on the slide clamp to lock the slide clamp in the second position to maintain the tube in the occluded state. The door of the pumping apparatus interacts with the slide clamp to move the slide clamp from the first, flowing position to the second, occluding position when the pumping apparatus is opened. The door also interacts with the slide clamp to move the slide clamp from the occluding position to the open position when the door is shut.

13 Claims, 3 Drawing Sheets

TWO STEP IV FLUID FLOW STOP

FIELD OF INVENTION

This invention is in the field of intravenous (IV) infusion devices such as peristaltic pumps and the associated flexible IV tubing and other related devices. Specifically, this invention pertains to devices used to prevent free flow in an IV tube when the infusion pump is disengaged from the IV tube.

BACKGROUND OF THE INVENTION

It is a common practice to deliver fluids such as medications to a patient intravenously by means of a pumping device such as a peristaltic pump. Such pumps are useful because they can deliver the medication in a highly controlled fashion, and because they do so without coming in contact with the medication. The fluid is moved through a flexible IV tube by pressing a pumping member against the tube sufficiently to occlude the tube, and then moving the pumping member along the tube to advance the fluid which is trapped downstream of the occlusion.

After the pumping member completes a stroke, a second pumping member repeats the process by occluding the tube and moving a second captured quantity of fluid along behind the first. The distance between occlusions and the speed of movement of the pumping members can be precisely controlled to effectively control the rate of infusion of the fluid into the patient. The IV tube is at all times occluded by one of the pumping members, thereby preventing "free flow" of fluid, by means other than the action of the pumping members.

It is common for the peristaltic pumping mechanism to be housed in a housing with a hinged door. The tube through which the fluid is to be moved is placed in contact with the pumping mechanism inside the door, with the ends of the tubing typically extending out the top and bottom of the door opening. As the door is shut over the tube, a platen on the inside of the door presses against the IV tube to provide a backing surface against which the pumping members can occlude the tube.

This arrangement of the IV tube relative to the pumping mechanism requires that there be some means for preventing flow in the tube when the door is open. Otherwise, during the process of setting up or dismantling the infusion apparatus, unwanted flow of fluid could occur in the IV tube. This could result in the uncontrolled infusion of medication into the patient under the influence of the static head in the tube, or blood from the patient could flow back into the IV tube. Known devices for preventing unwanted flow in the tube include manual clamps separate from the infusion pump, and automatic occluding devices mounted on the pump.

The manual devices require some manipulation skill on the part of the attending technician, and there is always the chance that the technician will forget to properly time the occlusion of the tube relative to the opening of the door on the pumping device. Furthermore, the door may be accidentally opened, resulting in free flow in the tube.

The known automatic devices mounted on the infusion pump are not uniformly reliable in timing the occlusion and release of the tube with the disengagement and engagement, respectively, of the pumping members. Typically, the action of opening the door is relied on to initiate the occlusion of the IV tube, and the action of closing the door is relied on to initiate the release of the IV tube. Therefore, at least momentary free flow of fluid can occur in some of these devices, or very accurate and repetitive alignment of the operative surfaces of the occlusion mechanism can be required. Some known devices also will allow the occluding device in the pump to be independently disengaged, whether by accident or on purpose, without the door being closed. This obviously results in the free flow of fluid.

Therefore, the object of the present invention is to provide an apparatus which will automatically and positively occlude an IV tube before the pumping mechanism is disengaged from the tube. A further object of the present invention is to provide an apparatus which will automatically and positively maintain the IV tube in an occluded state until after the pumping mechanism is engaged with the tube. A still further object is to provide an apparatus which will reliably occlude the IV tube, which is inexpensive to manufacture and easy to use.

SUMMARY OF THE INVENTION

The present invention, in its preferred embodiment, by, way of example, consists of a base member to which the IV tube is stationarily attached, and a slide clamp which slides relative to the base member and relative to the IV tube. A tubular tower is mounted on the base member to provide an attachment point for the IV tube. The tower is mounted with its longitudinal axis perpendicular to the main body of the base member, and the tower is hollow and open at both ends.

The open bottom end of the tower, which is the end attached to the base member, is sized to receive the IV tube within, in a liquid tight, structurally secure fit. Attachment of the tube within the tower can be by an interference fit or compression fit, and the attachment can be facilitated by gluing or other types of bonding. The IV tube exits the bottom of the tower and continues on toward the patient. A pumping tube is attached to the top of the tower, and the pumping tube extends through the pump mechanism, such as a peristaltic pump.

The slide clamp is slidingly mounted to the main body of the base member, with the relative sliding motion being in a direction oblique or perpendicular to the longitudinal axis of the tower. Therefore, the sliding motion is also oblique or perpendicular to the axis of the IV tube. The tube passes through an elongated aperture in the slide clamp, with the elongated dimension of the aperture being arranged parallel to the direction of the sliding motion. One end of the elongated aperture is a relatively open hole sized to receive the IV tube without constricting it, while the other end of the aperture is a relatively narrow slot sized to sufficiently constrict the IV tube to cause complete occlusion.

The exact location of the tube within the aperture is determined by the position of the slide clamp relative to the base member. The slide clamp has two functional positions in this respect. An occluding position is defined when the slide clamp is partially slidingly withdrawn from the base member. When the slide clamp is positioned in this occluding position, the IV tube passes through the end of the aperture which has the relatively narrow slot. An open position of the slide clamp is defined when the slide clamp does not fully occlude the tube. When the slide clamp is positioned in the full open position, the IV tube passes through the end of the aperture which has the relatively open hole.

At least one flexible cantilevered locking arm is formed on the base member, to interlock with a locking projection on the slide clamp. The locking arm is formed to lie generally parallel to the main body of the base member, and generally parallel to the direction of the siding motion. The free cantilevered end of the locking arm is biased toward the slide clamp. When the slide clamp is moved to its occluding position, the free end of the locking arm snaps in behind the locking projection on the slide clamp as it slides past, causing the locking arm to interlock with the locking projection. This prevents the slide clamp from returning from the occluding position to the open position, until the locking arm is released from the locking projection. A release tab projects from the locking arm to facilitate releasing the locking arm from the locking projection by pressing the tab toward the tower, thereby flexing the free end of the locking arm away from the slide clamp.

The flow stop is installed in a pumping apparatus so as to interact with a door or other moving mechanism on the pumping apparatus to move the slide clamp from its open position to its occluding position, or vice versa. Specifically, the door can have a boss or other feature positioned to contact the release tab as the door is shut, thereby releasing the locking arm from the locking projection.

The door can also have a latching mechanism which is activated after the door is shut, to push the slide clamp into full engagement with the base member after the boss on the door has released the locking arm. Finally, the door can have a hook or other means to hook onto a second projection on the slide clamp, to pull the slide clamp partially out of engagement with the base member before the door is opened, thereby occluding the IV tube. This hook can also be formed on the latching mechanism, so that as the latch is set, the slide clamp is moved to the open position, and as the latch is released, the slide clamp is moved to the occluding position. Both movements of the slide clamp are therefore achieved while the door is shut, and while the pumping mechanism is engaged with the pumping tube.

Therefore, as the latch is released, prior to opening the door, the hook on the latch contacts a projection on the slide clamp and pulls the slide clamp partially out of the base member, thereby occluding the IV tube. This prevents free flow of fluid in the IV tube when the door is subsequently opened and the pump is disabled. When the door is shut to resume operation of the pump, the boss on the door presses on the release tab, followed by the latch mechanism being engaged to push the slide clamp into engagement with the base member, thereby allowing the tube to open. This allows flow of fluid in the IV tube as the pump operates.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
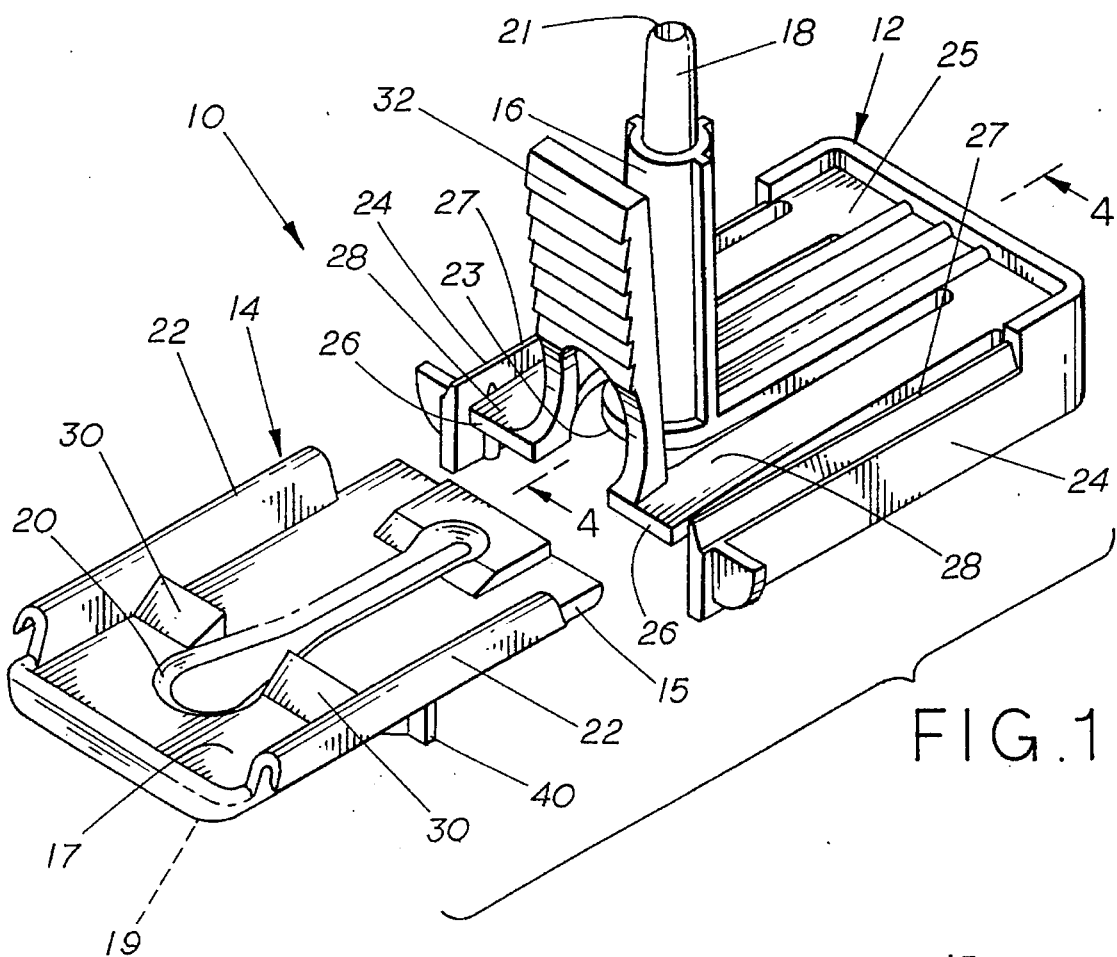
FIG. 1 is a perspective view of the flow stop of the present invention, showing the slide clamp fully withdrawn from the base.

As shown in FIG. 1, the flow stop 10 consists generally of a relatively open, box shaped base 12 and a mating slide clamp 14. Both parts can be formed by injection molding from various plastic materials. The solid rectangular body 15 of the slide clamp 14 is shaped and sized to fit slidingly within the base 12. The base 12 has a tower 16 formed on the top surface 25 of the base 12, with the tower 16 extending upwardly from the base 12, substantially perpendicular to the base 12. The top end 21 of the tower 16 is formed as a male tube connector 18 over which a pumping tube can be attached. The pumping tube can be attached by other means if desired. The open bottom end 23 of the tower 16 is attached to the base 12, and it is formed as a female tube connector into which an IV tube can be attached. The IV tube and the pumping tube can be the same tube if desired, simply passing through the tower.

The body 15 of the slide clamp 14 is penetrated from its top surface 17 to its bottom surface 19 by an elongated aperture 20. The elongated dimension of the aperture 20 is arranged on the slide clamp 14 to be parallel to the direction of the relative sliding movement between the base 12 and the slide clamp 14. Two side edges of the body 15 of the slide clamp 14 are fitted with rails 22 which lie parallel to the direction of the relative sliding movement. When the slide clamp 14 is slidingly engaged with the base 12, the rails 22 fit in a sliding fashion up through two rail channels 27 in the top of the base 12 and over two frames 24 formed on the edge of the base 12. Alignment of the slide clamp 14 with the base 12 is accomplished by the fit of the rails 22 over the frames 24, and by the fit of the body 15 of the slide clamp 14 between the frames 24.

Two flexible cantilevered locking arms 28 are molded into the top of the base 12, with their distal free ends 26 biased downwardly below the top surface 25 of the base 12. Biasing of the free ends 26 downwardly is accomplished by molding the locking arms 28 in a downwardly sloped configuration, but the biasing could also be accomplished by the use of springs or other means. A release tab 32 is formed on the locking arms 28, projecting upwardly from the locking arms 28 substantially parallel to the longitudinal axis of the tower 16. In the free state, when the locking arms 28 are sloped downwardly relative to the top surface 25 of the base 12, the release tab 32 is spaced away from the outer surface of the tower 16. The free ends 26 of the locking arms 28 can be flexed upwardly by pressing the release tab 32 toward the tower 16. Without departing from the spirit of the invention, one locking arm 28 can be used in place of the two shown, or each locking arm 28 can have a separate release tab 32.

Two locking projections 30 are molded on the top surface 17 of the body 15 of the slide clamp 14, with the projections 30 taking the form of ramps. The locking projections 30 are transversely positioned on the slide clamp 14 to align with the free ends 26 of the locking arms 28 when the slide clamp 14 is inserted into the base 12. The locking projections 30 are also longitudinally positioned to prevent the slide clamp 14 from being inserted into the base 12 far enough to move from its occluding position to its open position.

Figure 2:
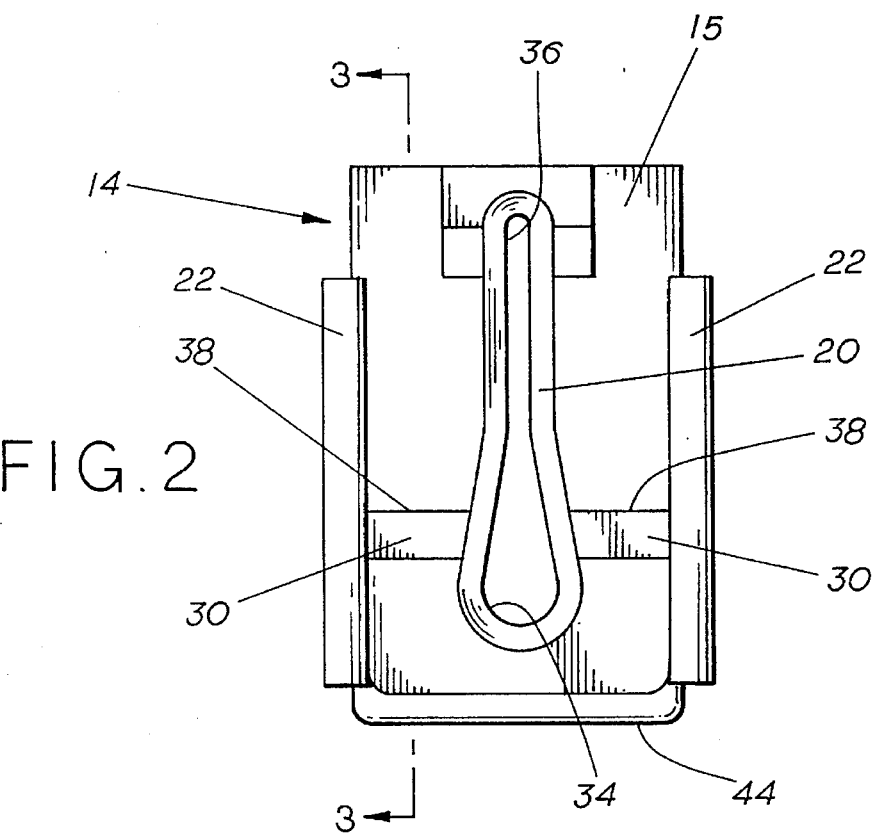
FIG. 2 is a plan view of the top of the slide clamp shown in FIG. 1.

As seen in FIG. 2, the elongated aperture 20 through the slide clamp 14 has an open end 34 shaped essentially as a round hole with a sufficiently large diameter to allow a selected IV tube to pass through the open end 34 without being occluded. Preferably, the diameter of the open end 34 is large enough to allow the IV tube to remain unrestricted. The other end of the aperture 20 is a relatively narrow slot 36. The width of the slot 36 is sufficiently small that a selected IV tube passing through the slot 36 would be completely occluded and would remain occluded against a foreseeable range of fluid pressures in the IV tube. The range of pressure against which the tube would remain occluded would include at least the static head anticipated during normal use of the infusion apparatus.

Figure 3:
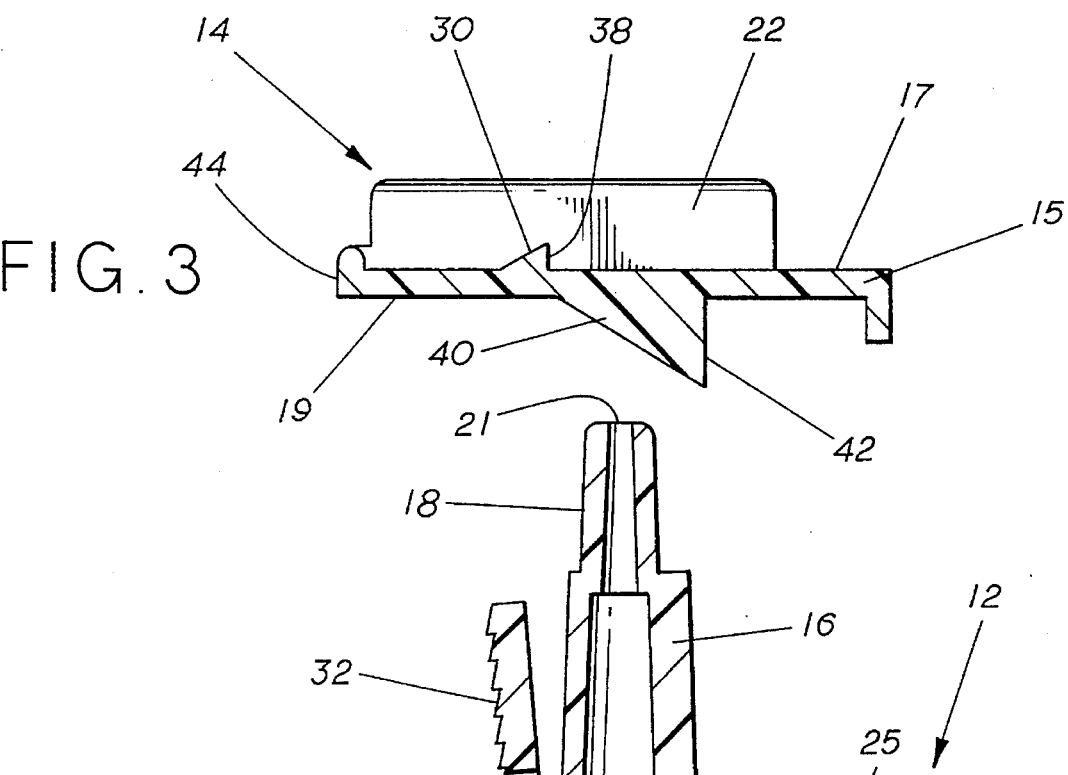
FIG. 3 is a section view of the slide clamp shown in FIG. 1, taken along the line 3—3.

As seen in FIG. 3, the locking projections 30 project upwardly from the top surface 17 of the body 15 of the slide clamp 14, presenting a substantially vertical locking face 38 to engage the free ends 26 of the locking arms 28, when the slide clamp 14 is in its occluding position. One or more pulling projections 40 project downwardly from the bottom surface 19 of the body 15. Each of the pulling projections 40 presents a substantially vertical pulling face 42 which will interact with the latch on the door of the pump housing (not shown) to pull the slide clamp 14 partially out of engagement with the base 12 before the door is opened. Pulling the slide clamp 14 partially out of the base 12 moves the slide clamp 14 from its open position to its occluding position. The body 15 of the slide clamp 14 also presents a substantially vertical pushing face 44 on one end, against which the door of the housing pushes to fully insert the slide clamp 14 into the base 12, after the door is closed. Pushing the slide clamp 14 into full insertion with the base 12 moves the slide clamp 14 from its occluding position to its open position.

Figure 4:
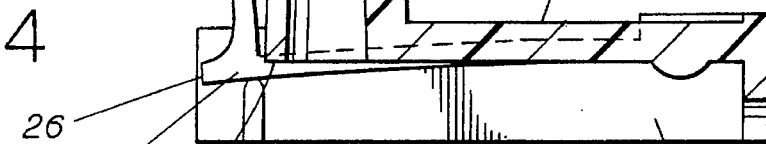
FIG. 4 is a section view of the base shown in FIG. 1, taken along the line 4—4.
Figure 5:
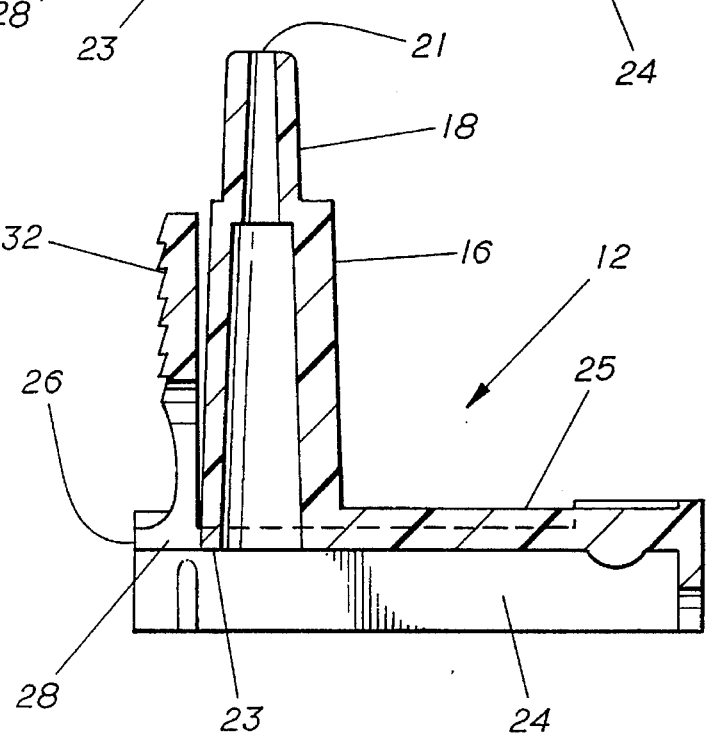
FIG. 5 is a section view of the base shown in FIG. 1, taken along the same line as FIG. 4, showing the release tab pressed against the tower.

FIG. 4 illustrates the downward slope of the locking arms 28 which is molded into the locking arms 28 to create the necessary downward bias to engage the free ends 26 of the locking arms 28 with the locking faces 38 on the locking projections 30. The separation between the release tab 32 and the side of the tower 16 can also be seen, as it exists when the locking arms are unrestrained. FIG. 5 shows the upwardly flexed position of the free ends 26 of the locking arms 28 which results from pressing the release tab 32 toward the tower 16. In this view, the release tab 32 is shown contacting the tower 16, but it should be understood that the free ends 26 can be flexed upwardly a sufficient amount to release the locking arms 28 from the locking projections 30, without actually causing the release tab 32 to contact the tower 16.

Figure 6:
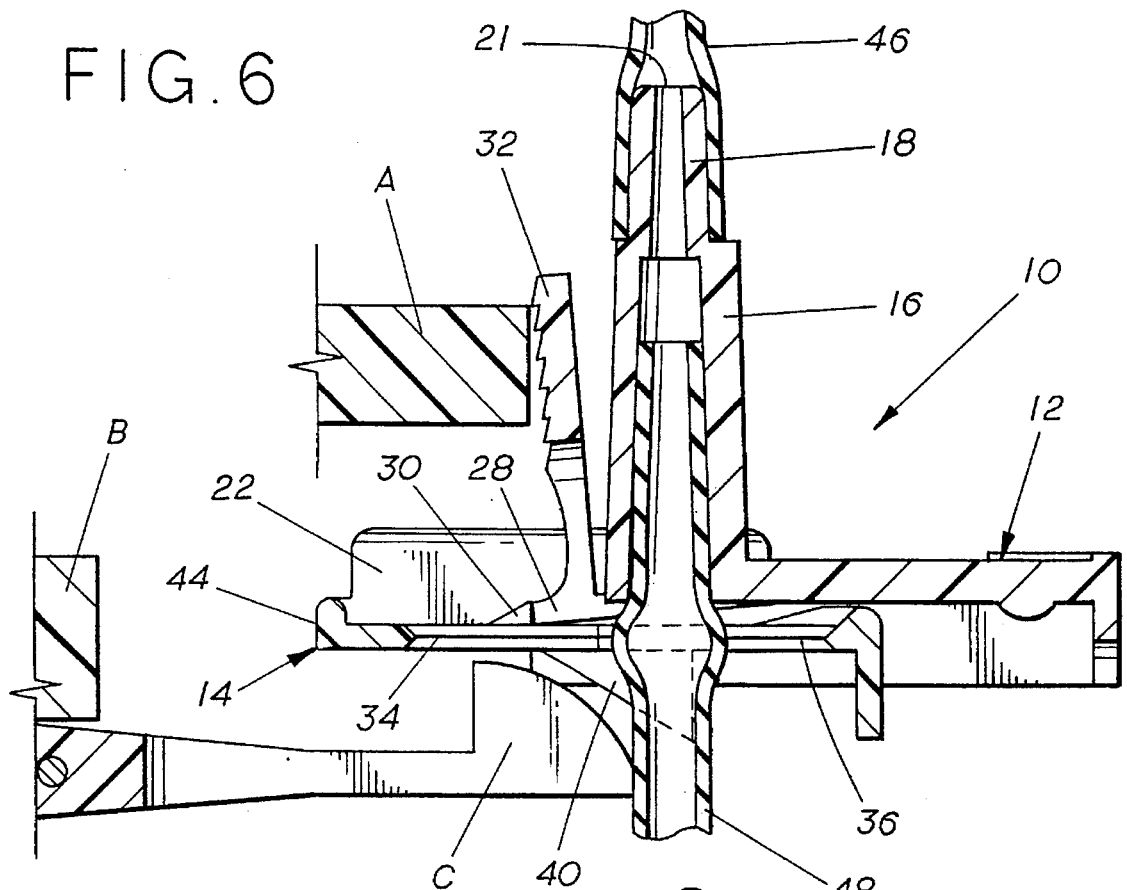
FIG. 6 is a section view of the device shown in FIG. 1, showing the slide clamp locked in the occluding position.
Figure 7:
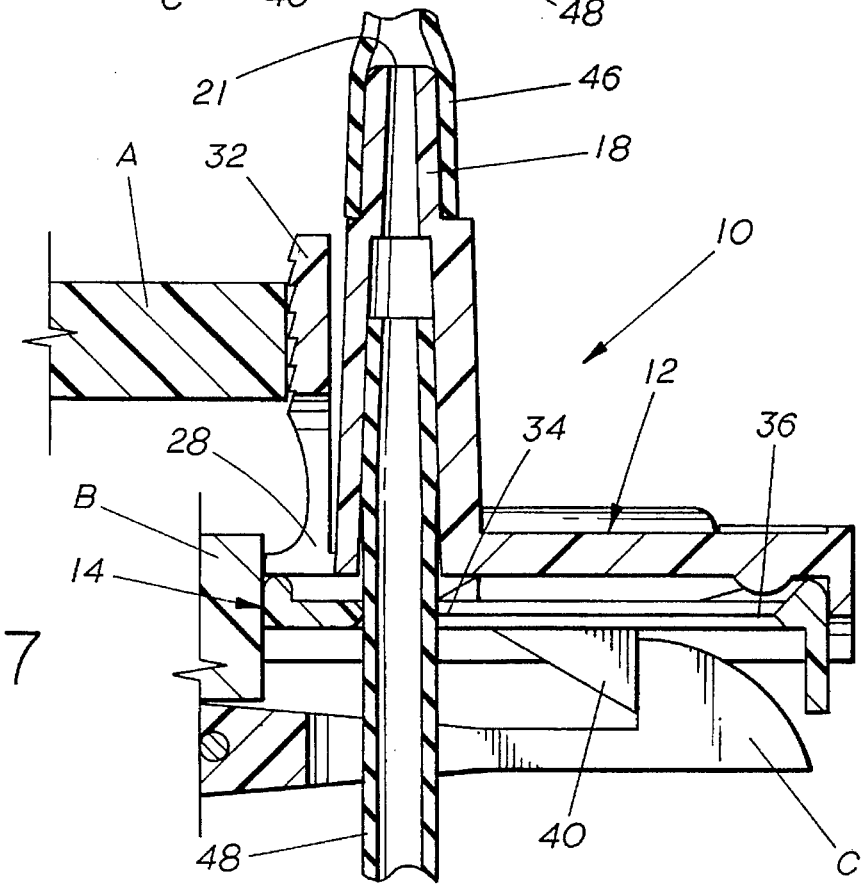
FIG. 7 is a section view of the device shown in FIG. 1, with the slide clamp in the open position.

FIGS. 6 and 7 show in general how the flow stop 10 of the present invention interacts with the door of the pump housing. FIG. 6 shows the slide clamp 14 in its occluding position relative to the base 12, with the slide clamp 14 partially withdrawn from the base 12 and the free ends 26 of the locking arms 28 engaging the locking projections 30 to hold the slide clamp 14 in its occluding position. This position of the slide clamp is achieved before the door is opened and maintained until after the door is closed. FIG. 7 shows the slide clamp 14 in its open position, with the slide clamp 14 fully inserted within the base 12 and the free ends 26 of the locking arms 28 flexed upwardly a sufficient amount to clear the locking projections 30.

Operative elements of the door and latch mechanism are shown schematically and designated as elements A, B, and C, to illustrate their interaction with the flow stop of the present invention. A releasing boss A can be formed on the door and positioned to contact the release tab 32 as the door is moved to the shut position, and to press the release tab 32 toward the tower 16. A pushing boss B can be formed on the latch mechanism and positioned to contact the pushing face 44 on the slide clamp 14 as the latch is engaged to push the slide clamp 14 from its occluding position to its open position, Finally, one or more pulling hooks C can be formed on the latch mechanism and positioned to contact the pulling projections 40 as the latch is disengaged to pull the slide clamp 14 from its open position to its occluding position.

Element A of the door moves generally to the right as seen in the Figures when the door is moved to the shut position. Elements B and C of the latch mechanism can be made to move generally to the left as seen in the Figures when the latch is being disengaged, and to the right when the latch is being engaged, it being understood that other elements (not shown) of the latch mechanism perform the actual latching of the door in the shut position. In addition, pulling hooks C can rotate in the clockwise direction from the position shown, relative to the remainder of the latch mechanism, against a spring bias.

OPERATION

To use the flow stop 10 of the present invention, the slide clamp 14 is fully inserted into the base 12 until the open end 34 of the aperture 20 aligns with the longitudinal axis of the tower 16. The release tab 32 is manually pressed toward the tower 16 as necessary to allow full insertion of the slide clamp. A pumping tube 46 is selected for its appropriate size, flexibility, and durability. One end of the selected pumping tube 46 is attached to the tube connector 18 at the top end 21 of the tower 16 by being fit over the tube connector 18. One end of a selected IV tube 48 is threaded through the open end 34 of the aperture 20 and attached to the base 12 by being fit into the bottom end 23 of the tower 16. The slide clamp 14 is then manually withdrawn from the base 12 to occlude the IV tube 48.

The other end of the pumping tube 46 is connected to a supply (not shown) of the chosen fluid to be pumped. The door of the pump housing is opened and the flow stop 10 is placed inside the door with the base 12 securely mounted to the pump housing and the free ends 26 of the locking arms 28 projecting outwardly from the pump housing. The pumping tube 46 is placed in contact with the pumping mechanism, and the door is shut. FIG. 6 shows the slide clamp 14 in its occluding position, with the release boss A about to contact the release tab 32 as the door is shut. As the door is completely shut, the releasing boss A presses the release tab 32 toward the tower 16, flexing the locking arms 28 upwardly. After the door is shut, the latching mechanism is latched, causing the pushing boss B to push the slide clamp 14 to its open position. FIG. 7 shows the slide clamp 14 in its open position, with the pulling hooks C having pivoted behind the pulling projections. The pump can then be operated in the conventional fashion to purge the IV tube 48 of air, and the IV tube 48 can be connected to a venous access site.

If the pump door is to be opened, the latching mechanism must first be disengaged, which will move the elements B and C to the left, causing the pulling hooks C to contact the pulling projections 40 and pull the slide clamp 14 to the left, to its occluding position. The latching mechanism can be constructed by known means so that only after this occlusion occurs will the door be unlatched. At this time, the door can be opened. The locking arms 28, having engaged the locking projections 30, maintain the slide clamp 14 in its occluding position, even if the slide clamp 14 is pushed toward the base 12 with considerable force.

The latching mechanism can also be constructed by known means so that when the door has been unlatched, the latching mechanism can not be moved back to its latched position until the door has been shut. Therefore, if the door is to be shut, the releasing boss A will press the release tab 32 toward the tower 16 to release the locking arms 28 from engagement with the locking projections 30, and the slide clamp 14 can be subsequently moved to the open position as explained before.

While the particular Two Step IV Fluid Flow Stop as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A mechanism for selectively preventing fluid flow through a resilient tube, comprising:

a base for holding said tube;

a fluid passageway formed in said base, said tube being connected in fluid communication with said passageway;

a slide clamp slidably mountable on said base for movement between an occluding position and an open position;

an aperture formed in said slide clamp for receiving said tube therethrough;

a substantially constricted region formed in said aperture, said constricted region occluding said tube to prevent fluid flow through said tube when said slide clamp is in said occluding position;

a substantially open region formed in said aperture, said open region allowing fluid flow through said tube when said slide clamp is in said open position; and a flexible cantilevered locking arm mounted on said base, said locking arm having a tab formed thereon, said locking arm being biased toward a locking position wherein said locking arm engages said slide clamp to prevent movement of said slide clamp from said occluding position to said open position, and said tab being moveable to deflect said locking arm toward a released position, wherein said locking arm is disengaged from said slide clamp to allow subsequent movement of said slide clamp from said occluding position to said open position.

2. A mechanism as recited in claim 1, wherein:

said aperture is tear-drop shaped;

said substantially constricted region is an elongated slot portion;

said substantially open region is a substantially round portion;

said tube is located in said slot portion when said slide clamp is in said occluding position; and said tube is located in said round portion when said slide clamp is in said open position.

3. A mechanism as recited in claim 1, further comprising a plurality of flexible cantilevered locking arms mounted on said base, each said locking arm being biased toward a respective locking position, wherein said locking arm engages slide clamp to prevent movement of said slide clamp from said occluding position to said open position, and each said locking arm being deflectable toward a released position, wherein said locking arm is disengaged from said slide clamp to allow subsequent movement of said slide clamp from said occluding position to said open position.

4. A method for selectively establishing fluid flow through a resilient tube, comprising the steps of:

providing a holding means for holding said tube;

providing said holding means with a fluid passageway through said holding means;

connecting said tube in fluid communication with said passageway;

providing an occluding means mounted on said holding means for movement between an occluding position, wherein said tube is occluded, and an open position, wherein said tube is open;

providing a locking means on said holding means for locking said occluding means in said occluding position;

providing a tab extending from said locking means for disengaging said locking means from said occluding means; and moving said tab to disengage said locking means from said occluding means; and moving said occluding means away from said occluding position.

5. A method as recited in claim 4, wherein said step of moving said tab to disengage said locking means further comprises the step of manually moving said tab.

6. A method as recited in claim 4, which further comprises the steps of:

providing an IV infusion pump, with a housing which has a door mounted on said housing and a handle on said door;

positioning said holding means within said housing;

moving said door into engagement with said locking means to move said tab, thereby disengaging said locking means from said occluding means; and moving said handle into engagement with said occluding means to move said occluding means from said occluding position to said open position.

7. A mechanism for selectively preventing fluid flow through a resilient tube, comprising:

a base for positioning said tube, said base having a fluid passageway, said tube being connected in fluid communication with said passageway;

a slide clamp slidably mountable on said base and moveable thereon between an occluding position and an open position, for engagement with said tube to selectively occlude said tube;

a flexible cantilevered arm formed on said base, said flexible arm being engageable with said slide clamp to selectively prevent movement of said slide clamp from said occluding position to said open position; and a tab formed on said flexible arm, for releasing said flexible arm from said slide clamp, to allow subsequent movement of said slide clamp from said occluding position to said open position; wherein:

said slide clamp is formed with an aperture for receiving said tube therethrough;

said tube passes through a first occluding region of said aperture to prevent fluid flow through said tube, when said slide clamp is in said occluding position;

said tube passes through a second open region of said aperture to allow fluid flow through said tube, when said slide clamp is in said open position;

said flexible arm is biased toward a locking position, wherein said flexible arm engages said slide clamp to prevent movement of said slide clamp from said occluding position to said open position; and said tab is movable to deflect said flexible arm toward a released position, wherein said flexible arm is disengaged from said slide clamp.

8. A mechanism as recited in claim 7, wherein:

said first occluding region of said aperture is formed as an elongated slot sized to occlude said tube; and said second open region of said aperture is formed as a substantially round shape sized to allow said tube to remain open.

9. A mechanism for selectively preventing fluid flow through a resilient tube, comprising:

a base for positioning said tube;

a slide clamp slidably mountable on said base and moveable thereon between an occluding position and an open position, for engagement with said tube to selectively occlude said tube;

a locking projection formed on said slide clamp;

a flexible cantilevered arm formed on said base, said flexible arm being engageable with said locking projection to selectively prevent movement of said slide clamp from said occluding position to said open position; and a releasing means formed on said flexible arm, for releasing said flexible arm from said slide clamp, to allow subsequent movement of said slide clamp from said occluding position to said open position; wherein:

said slide clamp is formed with an aperture for receiving said tube therethrough;

said tube passes through a first occluding region of said aperture to prevent fluid flow through said tube, when said slide clamp is in said occluding position;

said tube passes through a second open region of said aperture to allow fluid flow through said tube, when said slide clamp is in said open position;

said flexible arm is biased toward a locking position, wherein said flexible arm engages said locking projection to prevent movement of said slide clamp from said occluding position to said open position; and said flexible arm is deflectable toward a released position, wherein said flexible arm is disengaged from said locking projection.

10. A mechanism as recited in claim 9, wherein:

said first occluding region of said aperture is formed as an elongated slot sized to occlude said tube; and said second open region of said aperture is formed as a substantially round shape sized to allow said tube to remain open.

11. A mechanism for selectively preventing fluid flow through a resilient tube, comprising:

a base for positioning said tube;

a slide clamp formed with an aperture for receiving said tube therethrough, said slide clamp being slidably mounted on said base and moveable thereon between an occluding position, wherein said aperture occludes said tube to prevent fluid flow through said tube, and an open position, wherein said aperture allows fluid flow through said tube;

a plurality of limit means formed on said slide clamp;

a plurality of flexible cantilevered arms formed on said base, each said flexible arm being biased toward a respective locking position, wherein said flexible arm engages one of said limit means to selectively prevent movement of said slide clamp from said occluding position to said open position; and at least one tab formed on said flexible arms, for deflecting said flexible arm toward a respective released position, wherein said flexible arm is disengaged from said limit means to allow subsequent movement of said slide clamp from said occluding position to said open position.

12. A mechanism for selectively preventing fluid flow through a resilient tube, comprising:

a base for holding said tube;

a slide clamp slidably mountable on said base for movement between an occluding position and an open position;

a locking projection formed on said slide clamp;

an aperture formed in said slide clamp for receiving said tube therethrough;

a substantially constricted region formed in said aperture, said constricted region occluding said tube to prevent fluid flow through said tube when said slide clamp is in said occluding position;

a substantially open region formed in said aperture, said open region allowing fluid flow through said tube when said slide clamp is in said open position; and a flexible cantilevered locking arm mounted on said base, said locking arm being biased toward a locking position wherein said locking arm engages said locking projection to prevent movement of said slide clamp from said occluding position to said open position, and said locking arm being deflectable toward a released position, wherein said locking arm is disengaged from said locking projection to allow subsequent movement of said slide clamp from said occluding position to said open position.

13. A mechanism as recited in claim 12, wherein:

said aperture is tear-drop shaped;

said substantially constricted region is an elongated slot portion;

said substantially open region is a substantially round portion;

said tube is located in said slot portion when said slide clamp is in said occluding position; and said tube is located in said round portion when said slide clamp is in said open position.

* * * * *